(12) United States Patent
Fischer

(10) Patent No.: US 9,040,053 B2
(45) Date of Patent: May 26, 2015

(54) HER2 DNA VACCINE AS ADJUNCT TREATMENT FOR CANCERS IN COMPANION ANIMALS

(75) Inventor: Laurent Bernard Fischer, Sainte Foy les Lyon (FR)

(73) Assignee: MERIAL, INC., Duluth, GA (US)

( * ) Notice: Subject to any disclaimer, the term of this patent is extended or adjusted under 35 U.S.C. 154(b) by 0 days.

(21) Appl. No.: 13/272,651

(22) Filed: Oct. 13, 2011

(65) Prior Publication Data

US 2012/0093841 A1 Apr. 19, 2012

Related U.S. Application Data

(60) Provisional application No. 61/394,505, filed on Oct. 19, 2010.

(51) Int. Cl.
| | | |
|---|---|---|
| A61K 39/00 | (2006.01) | |
| A61P 35/00 | (2006.01) | |
| C12N 15/85 | (2006.01) | |
| A61M 37/00 | (2006.01) | |

(52) U.S. Cl.
CPC ......... A61K 39/0011 (2013.01); *A61K 2039/53* (2013.01); *A61K 2039/545* (2013.01)

(58) Field of Classification Search
CPC .................................................. A01B 12/006
See application file for complete search history.

(56) References Cited

U.S. PATENT DOCUMENTS

| | | | |
|---|---|---|---|
| 6,328,969 B1 | 12/2001 | Houghton et al. | |
| 7,556,805 B2 | 7/2009 | Houghton et al. | |
| 2002/0150589 A1 | 10/2002 | Houghton | |
| 2011/0142791 A1* | 6/2011 | Shahabi | 424/85.1 |

FOREIGN PATENT DOCUMENTS

WO WO 2006036550 A2 4/2006

OTHER PUBLICATIONS

Peruzzi et al. (Vaccine. 2010; 28:1201-1208 [Available online Nov. 26, 2009]).*
Disis et al. (Immunology 1998; 93: 192-199).*
Tu et al. (Vaccine. 2007; 25:719-728).*
Singer et al. (Mol Immunol. Apr. 2012; 50(4-3): 200-209.*
Peruzzia, Daniela et al. Telomerase and HER-2/neu as targets of genetic cancer vaccines in dogs. Vaccine 28 (2010) 1201-1208.
Gallo, Pasquale et al. Xenogeneic Immunization in Mice Using HER2 DNA Delivered by an Adenoviral Vector. Int. J. Cancer: 113, 67-77 (2005).
Jacob, JB et al. Cancer Research. "Combining Human and Rat Sequences in Her-2 DNA Vaccines Blunts Immune Tolerance and Drives Antitumor Immunity." 70(1) Jan. 1, 2010.
Norell, H et al. Journal of Translational Medicine. "Vaccination with a plasmid DNA encoding HER-2/neu together with low doses of GM-CSF and IL-2 in patients with metastatic breast carcinoma: a pilot clinical trial." 2010, 8:53.
Orlandi, F et al. Cancer Therapy: *Preclinical.* "Antibody and CD8+ T Cell Responses against HER2/neu Required for Tumor Eradication after DNA Immunization with a Flt-3 Ligand FusionVaccine." 2007;6195 13(20) Oct. 15, 2007.
Quaglino E et al. "Concordant morphologic and gene expression data show that a vaccine halts HER-2/neu preneoplastic lesions" Journal Clinical Investigations. vol. 113 No. 5 Mar. 2004.
De Maria et al., 2005 Spontaneous Feline Mammary Carcinoma is a Model of Her2 Overexpressing Poor Prognosis Human Breast Cancer; Cancer Res 2005: 65 (3); 907-912.
Winston et al., 2005 Immunohistochemical detection of Her2/neu expression in spontaneous feline mammary tumours; Veterinary and Comparative Oncology 3, 1, 8-15, 2005.
Rungsipipat et al., 2008 C-erbB-2 oncogene and P21WAF/CIPI tumor suppressor gene expression as prognostic factors in canine mammary adenocarcinomas; Comp Clin Pathol 2008, 17:35-41.
Chang et al., 2004 Enhanced efficacy of DNA vaccination against Her2/neu tumor antigen by genetic adjuvants; IJC vol. 111 pp. 86-95, Aug. 10, 2004.
Pupa et al., 2005 HER2: A biomarker at the crossroads of breast cancer immunotherapy and molecular medicine. JCP vol. 205 pp. 10-18, May 10, 2005.
S. Barclay et al., "Rapid isolation of monoclonal antibodies specific for cell surface differentiation antigens", Proc. Natl. Acad. Sci. USA, 1986 vol. 83, pp. 4336-4340.
S. Krishnan et al., "Paving the way towards DNA vaccines", Nature Medicine, 1995, vol. 1, No. 6, pp. 521-522.
S. Park, "JL1, a Novel Differentiation Antigen of Human Cortical Thymocyte", J. Exp. Med., The Rockefeller University Press, 1993, vol. 178, pp. 1447-1451.
S. Vijayasaradhi et al., "Intracellular Sorting and Targeting of Melanosomal Membrane Proteins: Identification of Signals for Sorting of the Human Brown Locus Protein, GP75", JCB, 1995, v130, 4, 807-820.
S. Vijayasaradhi et al., "The Melanoma Antigen gp75 is the Human Homologue of the Mouse b (Brown) Locus Gene Product", J. Exp. Med., 1990, vol. 171, pp. 1375-1380.
Verma and Somia. Gene and therapy-promises, problems and prospects. Nature 389: 239-242, Sep. 1997.
Zhai et al. Antigen-Specific Tumor Vaccines. The Journal of Immunology 156: 700-710, Jan. 1996.
Philibert JC et al. Influence of Host Factors on Survival in Dogs with Malignant Mammary Gland Tumors; J Vet Intern Med 2003; 17:102-106.
Press MF et al. Expression of the Her2/neu proto-oncogene in normal human adult and fetal tissues; Oncogene, 1990. 5: pp. 953-962.

(Continued)

*Primary Examiner* — Scott Long
(74) *Attorney, Agent, or Firm* — Judy Jarecki-Black; Chad Kitchen; Merial, Inc.

(57) ABSTRACT

The application discloses therapeutic vaccines based upon the "pING" DNA plasmid vector expressing the gene encoding the rat Her2 protein. Vaccines according to the instant disclosure are used as an adjunct treatment for surgery, radiation and/or chemotherapy for dogs and cats with cancers that over express the Her2 antigen, and prolong the post-surgical disease free interval and/or survival time. Also included are therapeutically effective methods of immunization using said vaccines.

11 Claims, 7 Drawing Sheets

(56) References Cited

OTHER PUBLICATIONS

Miller and Vile. Targeted vectors for gene therapy. FASEB J. 9: 190-199, 1995.

N. Nanda et al., "Induction of Anti-Self-Immunity to Cure Cancer", Cell, 1995, v82, p. 13-17.

Deonarain, M. Ligand-targeted receptor-mediated vectors for gene delivery. Exp. Opin. Ther. Patents 8(1): 53-69, 1998.

Disis et al. Peptide-based, but not whole protein, vaccines elicit immunity to HER2/neu, an oncogenic self-protein. The Journal of Immunology 156: 3151-3158, May 1, 1996.

Eck et al. (Gene Based Therapy in the Pharmacological Basis of Therapeutics, Goodman and Gilman, Eds, 1996, pp. 77-101).

F. Ausubel et al., "Expression of Proteins is Insect Cells using Baculoviral Vectors", Current Protocols in Molecular Biology, Greene Publishing and Wiley-Interscience, 1990, vol. 8, 16.8.1-16.11-7.

G. Adema et al., "Molecular Characterization of the Melanocyte Lineage-specific Antigen gp100", The Journal of Biology Chemistry, The American Society for Biochemistry and Molecular Biology, 1994, vol. 269, No. 31, pp. 20126-20133.

J. Rowell et al., "Lysosome-Associated Membrane Protein-1-Mediated Targeting of the HIV-1 Envelope Protein to an Endosomal/Lysosomal Compartment Enhances Its Presentation to MHC Class II-Restricted T Cells", The American Association of Immunologists, 1995, pp. 1818-1828.

J. Ulmer et al., "Heterologous Protection Against Influenza by Injection of DNA Encoding a Viral Protein", Science, 1993, vol. 259, pp. 1745-1749.

Crystal. Transfer of Genes to Humans: Early Lessons and Obstacles to Success. Science 270: 404-410, Oct. 20, 1995.

D. Pardoll et al., "Exposing the Immunology of Naked DNA Vaccines", Immunity, Cell Press, 1995, vol. 3, pp. 165-169.

A. Houghton et al., "Recognition of Autoantigens by Patients with Melanoma", A. NY Acad. Sci.1993, 59-69.

Amici A. et al. Venanzi FM, Concetti A. Genetic immunization against neu/erbB2 transgenic breast cancer. Cancer Immunol Immunother 1998;47:183-90.

B. Bouchard et al., "Induction of Pigmentation in Mouse Fibroblasts by Expression of Human Tyrosinase cDNA", J. Exp. Med., 1989, vol. 169, pp. 2029-2042.

B. Bouchard et al., "Production and Characterization of Antibodies against Human Tyrosinase", The Journal of Investigative Dermatology, 1994, vol. 102, No. 3, pp. 291-295.

Bargmann et al. The neu oncogene encodes an epidermal growth factor receptor-related protein. Nature. Jan. 16-22, 1986;319(6050):226-30.

Bergman PJ et al. Long-Term Survival of Dogs with Advanced Malignant Melanoma after DNA Vaccination with Xenogeneic Human Tyrosinase: A Phase I Trial. CCR, vol. 9, 1284-1290, Apr. 2003.

Bernhard H et al. Vaccination against the HER2/neu oncogenic protein. E-R Cancer 9 (1) 33-44, 2002.

Berta, GN et al. Anti-HER2 DNA vaccine protects Syrian hamsters against squamous cell carcinomas. Br J Cancer, vol. 93(11), Nov. 28, 2005.

C. Cabanas et al., "Characterization of a CD11c-Reactive Monoclonal Antibody (HCI/I) Obtained by Immunizing with Phorbol Ester Differentiated U937 Cells", Hybridoma, 1988, vol. 7, No. 2, pp. 167-177.

C. Naftzger et al., "Immune response to a differentiation antigen induced by altered antigen: A study of tumor rejection and autoimmunity", Proc. Natl. Acad. Sci. USA, 1996, vol. 93, pp. 14809-14814.

C. Tiff et al., "The Folding and Cell Surface Expression of CD4 Requires Glycosylation", The Journal of Biological Chemistry, 1992, vol. 267, No. 5, pp. 3268-3273.

* cited by examiner

```
   1 ttggctattg gccattgcat acgttgtatc tatatcataa tatgtacatt
  51 tatattggct catgtccaat atgaccgcca tgttgacatt gattattgac
 101 tagttattaa tagtaatcaa ttacggggtc attagttcat agcccatata
 151 tggagttccg cgttacataa cttacggtaa atggcccgcc tggctgaccg
 201 cccaacgacc cccgcccatt gacgtcaatg atgacgtatg ttcccatagt
 251 aacgccaata gggactttcc attgacgtca atgggtggag tatttacggt
 301 aaactgccca cttggcagta catcaagtgt atcatatgcc aagtccgccc
 351 cctattgacg tcaatgacgg taaatggccc gcctggcatt atgcccagta
 401 catgacctta cgggactttc ctacttggca gtacatctac gtattagtca
 451 tcgctattac catggtgatg cggttttggc agtacaccaa tgggcgtgga
 501 tagcggtttg actcacgggg atttccaagt ctccacccca ttgacgtcaa
 551 tgggagtttg ttttggcacc aaaatcaacg ggactttcca aatgtcgta
 601 ataaccccgc cccgttgacg caaatgggcg gtaggcgtgt acggtgggag
 651 gtctatataa gcagagctcg tttagtgaac cgtcagatcg cctggagacg
 701 ccatccacgc tgttttgacc tccatagaag acaccgggac cgatccagcc
 751 tccgcggccg gaacggtgc attggaacgc ggattccccg tgccaagagt
 801 gacgtaagta ccgcctatag actctatagg cacacccctt tggctcttat
 851 gcatgctata ctgttttgg cttgggcct atacaccccc gcttccttat
 901 gctataggtg atggtatagc ttagcctata ggtgtgggtt attgaccatt
 951 attgaccact cccctattgg tgacgatact ttccattact aatccataac
1001 atggctcttt gccacaacta tctctattgg ctatatgcca atactctgtc
1051 cttcagagac tgacacggac tctgtatttt acaggatgg ggtcccattt
1101 attatttaca aattcacata taacaacg ccgtcccccg tgcccgcagt
1151 ttttattaaa catagcgtgg gatctccacg cgaatctcgg gtacgtgttc
1201 cggacatggg ctcttctccg gtagcggcgg agcttccaca tccgagccct
1251 ggtcccatgc ctccagcggc tcatggtcgc tcggcagctc cttgctccta
1301 acagtggagg ccagacttag gcacagcaca atgcccacca ccaccagtgt
1351 gccgcacaag gccgtggcgg tagggtatgt gtctgaaaat gagctcggag
1401 attgggctcg caccgctgac gcagatggaa gacttaaggc agcggcagaa
1451 gaagatgcag gcagctgagt tgttgtattc tgataagagt cagaggtaac
1501 tcccgttgcg gtgctgttaa cggtggaggg cagtgtagtc tgagcagtac
1551 tcgttgctgc cgcgcgcgcc accagacata atagctgaca gactaacaga
                NcoI (1611)    PstI (1624)
1601 ctgttccttt ccatggtct tttctgcagt caccgtccac gcgttaatac
1651 gactcactat agggagaccc aagctggcta cgtttaaac ttaagcttgg
                BamHI (1711)          EcoRI (1734)
1701 taccgagctc ggatccacta gtccagtgtg gtggaattcc gggaaga
```

FIG. 3

```
3338 aaggcttagg caatagagta gggccaaaaa gcctgacctc actctaactc
3388 aaagtaatgt ccaggttccc agagaatatc tgctggtatt tttctgtaaa
3438 gaccatttgc aaaattgtaa cctaatacaa agtgtagcct tcttccaact
3488 caggtagaac acacctgtct ttgtcttgct gttttcactc agcccttta
3538 acattttccc ctaagcccat atgtctaagg aaaggatgct atttggtaat
3588 gaggaactgt tatttgtatg tgaattaaag tgctcttatt ttaaaaaacc
3638 ggaattctgc agatatccag cacagtggcg gccgctcgag tctagagggc
3688 ccgtttaaac ccgctgatca gcctcgactg tgccttctag ttgccagcca
3738 tctgttgttt gcccctcccc cgtgccttcc ttgaccctgg aaggtgccac
3788 tcccactgtc ctttcctaat aaaatgagga aattgcatcg cattgtctga
3838 gtaggtgtca ttctattctg gggggtgggg tggggcagga cagcaagggg
3888 gaggattggg aagacaatag caggcatggt ggggatgcag gggggggggg
3938 gcgctgaggt ctgcctcgtg aagaaggtgt tgctgactca taccaggcct
3988 gaatcgcccc atcatccagc cagaaagtga gggagccacg gttgatgaga
4038 gctttgttgt aggtggacca gttggtgatt ttgaactttt gctttgccac
4088 ggaacggtct gcgttgtcgg gaagatgcgt gatctgatcc ttcaactcag
4138 caaaagttcg atttattcaa caaagccgcc gtcccgtcaa gtcagcgtaa
4188 tgctctgcca gtgttacaac caattaacca attctgatta gaaaaactca
4238 tcgagcatca aatgaaactg caatttattc atatcaggat tatcaatacc
4288 atatttttga aaaagccgtt tctgtaatga aggagaaaac tcaccgaggc
4338 agttccatag gatggcaaga tcctggtatc ggtctgcgat tccgactcgt
4388 ccaacatcaa tacaacctat taatttcccc tcgtcaaaaa taaggttatc
4438 aagtgagaaa tcaccatgag tgacgactga atccggtgag aatggcaaaa
4488 gcttatgcat ttctttccag acttgttcaa caggccagcc attacgctcg
4538 tcatcaaaat cactcgcatc aaccaaaccg ttattcattc gtgattgcgc
4588 ctgagcgaga cgaaatacgc gatcgctgtt aaaaggacaa ttacaaacag
4638 gaatcgaatg caaccggcgc aggaacactg ccagcgcatc aacaatattt
4688 tcacctgaat caggatattc ttctaatacc tggaatgctg ttttcccggg
4738 gatcgcagtg gtgagtaacc atgcatcatc aggagtacgg ataaaatgct
4788 tgatggtcgg aagaggcata aattccgtca gccagtttag tctgaccatc
4838 tcatctgtaa catcattggc aacgctacct tgccatgttt cagaaacaa
4888 ctctggcgca tcgggcttcc catacaatcg atagattgtc gcacctgatt
4938 gcccgacatt atcgcgagcc catttatacc catataaatc agcatccatg
                   XhoI (5006)
4988 ttggaattta atcgcggcct cgagcaagac gtttcccgtt gaatatggct
5038 cataacaccc cttgtattac tgtttatgta agcagacagt tttattgttc
5088 atgatgatat attttatct tgtgcaatgt aacatcagag attttgagac
                   PstI (5162)
5138 acaacgtggc tttccccccc ccccctgcag cgtttcttcc ttttccccac
```

FIG. 3 (continued)

```
5188 cccaccccccc aagttcgggt gaaggcccag ggctcgcagc caacgtcggg
5238 gcggcaggcc ctgccatagc ctcaggttac tcatatatac tttagattga
5288 tttaaaactt cattttaat ttaaaaggat ctaggtgaag atccttttg
5338 ataatctcat gaccaaaatc ccttaacgtg agttttcgtt ccactgagcg
5388 tcagaccccg tagaaaagat caaaggatct tcttgagatc ctttttttct
5438 gcgcgtaatc tgctgcttgc aaacaaaaaa accaccgcta ccagcggtgg
5488 tttgtttgcc ggatcaagag ctaccaactc ttttccgaa ggtaactggc
5538 ttcagcagag cgcagatacc aaatactgtt cttctagtgt agccgtagtt
5588 aggccaccac ttcaagaact ctgtagcacc gcctacatac ctcgctctgc
5638 taatcctgtt accagtggct gctgccagtg gcgataagtc gtgtcttacc
5688 gggttggact caagacgata gttaccggat aaggcgcagc ggtcgggctg
5738 aacggggggt tcgtgcacac agcccagctt ggagcgaacg acctacaccg
5788 aactgagata cctacagcgt gagctatgag aaagcgccac gcttcccgaa
5838 gggagaaagg cggacaggta tccggtaagc ggcagggtcg aacaggaga
5888 gcgcacgagg gagcttccag ggggaaacgc ctggtatctt tatagtcctg
5938 tcgggtttcg ccacctctga cttgagcgtc gatttttgtg atgctcgtca
5988 ggggggcgga gcctatggaa aaacgccagc aacgcggcct ttttacggtt
6038 cctggccttt tgctggcctt ttgctcacat gttctttcct gcgttatccc
6088 ctgattctgt ggataaccgt attaccgcca tgcattagtt attaatagta
6138 atcaattacg gggtcattag ttcatagccc atatatggag ttccgcgtta
                          BglI (6206)
6188 cataacttac ggtaaatggc ccgcctggct gaccgcccaa cgacccccgc
6238 ccattgacgt caataatgac gagatctgat ataggtgaca gacgatatga
6288 ggctatatcg ccgatagagg cgacatcaag ctggcacatg gccaatgcat
6338 atcgatctat acattgaatc aatattggca attagccata ttagtcattg
6388 gttatatagc ataaatcaat a
```

FIG. 3 (continued)

HER2 DNA VACCINE AS ADJUNCT TREATMENT FOR CANCERS IN COMPANION ANIMALS

CROSS-REFERENCE TO RELATED APPLICATIONS

This application claims benefit of U.S. provisional application Ser. No. 61/394,505, filed Oct. 19, 2010.

BACKGROUND OF THE INVENTION

This application relates to compositions for treatment of differentiation antigen-dependent cancers and to methods of using such compositions. The invention utilizes compositions containing xenogeneic differentiation antigens, which are associated with cancers to provide effective therapy.

Differentiation antigens are tissue-specific antigens that are shared by autologous and some allogeneic tumors of similar derivation, and on normal tissue counterparts at the same stage of differentiation. Differentiation antigens have been shown to be expressed by a variety of tumor types, including melanoma, leukemia, lymphomas, colorectal carcinoma, breast carcinoma, prostate carcinoma, ovarian carcinoma, pancreas carcinomas, and lung cancers. For example, differentiation antigens expressed by melanoma cells include Melan-A/MART-1, Pmel17, tyrosinase, and gp75. Differentiation antigen expressed by lymphomas and leukemia include CD 19 and CD20/CD20 B lymphocyte differentiation markers). An example of a differentiation antigen expressed by colorectal carcinoma, breast carcinoma, pancreas carcinoma, prostate carcinoma, ovarian carcinoma, and lung carcinoma is the mucin polypeptide muc-1. A differentiation antigen expressed by, for example, breast carcinoma is Her2 (synonyms: Her2/neu, ECBB2, ErbB2, c-erb-2), which is a gene coding for a tyrosine kinase receptor that is a member of the family of epidermal growth factor receptors (De Maria et al., 2005). Over expression of Her2 has been demonstrated in mammary gland tumors of both the cat (Winston et al., 2005) and the dog (Rungsipipat et al., 2008). Winston et al. (2005) used existing assay methods (HERCEPTEST™, Dako USA, Carpinteria, Calif.; NCL-CB11, Novocastra, Newcastle, UK) to successfully grade levels of Her2 expression on feline mammary tumors as 0=minimal/absent, 1=weak, 2=moderate, or 3=intense. The HERCEPTEST™ and NCL-CB11 assays identified 27 and 23 cats respectively, out of 30 examined, as having grade 2 or 3 Her2 expression in mammary tumor samples.

In addition to successfully grading levels of Her2 over expression in feline mammary tumors, Winston et al. (2005) used the HERCEPTEST™ to detect low levels of Her2 expression in normal feline epithelial tissues and cell types including: hair follicle, mammary gland, gastric pit, salivary gland duct, renal cortical and medullary tubules, colonic and small intestinal crypt, brain, pancreatic duct and islets, splenic macrophages, adrenal cortex, hepatocytes, and testicular Leydig's cells. Expression of Her2 has been documented on a range of human epithelial cell types including gastro-intestinal, respiratory, reproductive, urinary, skin, mammary and placenta (Press et al., 1990). These findings indicate that the expression of Her2 is common in a range of tissue types of humans and cats. The finding of Her2 over expression in dog mammary tumors suggests this species would share expression characteristics identified in humans and cats. Existing assays and reagents can serve as tools to screen expression levels of Her2 in companion animal cancers in order to justify treatment with the Her2 cancer vaccine.

Unfortunately, in most cases, the immune system of the individual is tolerant of such differentiation antigens, and fails to mount an effective immune response. Several technologies have been considered to address this challenge: (cytokines as genetic adjuvants (Chang et al., 2004), xenogeneic vaccination (Pupa et al., 2005), electrotransfer (Quaglino et al., 2004), combination with chemotherapy (Bernhardt et al., 2002). Although results were encouraging, greater efficacy was required for these approaches to be considered a key component of a first-line therapeutic strategy. Further, recent findings indicate both antibody and cell-mediated immunity are required for tumor eradication post immunization, perhaps explaining, in part, the lack of success in the field (Orlandi et al., 2007). Therefore, for the treatment of cancers where the tumor expresses differentiation antigens therefore, it would be desirable to have a method for stimulating a therapeutically effective immune response against the differentiation antigen in vivo. It an object of the present invention to provide such a method.

REFERENCES

Orlandi et al. Antibody and CD8$^+$ T cell Responses against HER2/neu Required for Tumor Eradication after DNA Immunization with a Flt-3 Ligand FusionVaccine. Clin Cancer Res 2007; 13(20) Oct. 15, 2007.

Amici A. et al. Venanzi F M, Concetti A. Genetic immunization against neu/erbB2 transgenic breast cancer. Cancer Immunol Immunother 1998; 47:183-90.

Bergman P J et al. Long-Term Survival of Dogs with Advanced Malignant Melanoma after DNA Vaccination with Xenogeneic Human Tyrosinase: A Phase I Trial. CCR, Vol. 9, 1284-1290, April 2003.

Bargmann et al. The neu oncogene encodes an epidermal growth factor receptor-related protein. Nature. Jan. 16-22; 319(6050):226-30.

Norell H et al. Vaccination with a plasmid DNA encoding HER2/neu together with low doses of GM-CSF and IL-2 in patients with metastatic breast carcinoma: a pilot clinical trial. JTM 7 Jun. 2010, 8:53.

Jacob, J B et al. Combining Human and Rat Sequences in Her2 DNA Vaccines Blunts Immune Tolerance and Drives Antitumor Immunity; Cancer Res Jan. 1, 2010 70; 119.

De Maria R et al. Spontaneous Feline Mammary Carcinoma is a Model of Her2 Overexpressing Poor Prognosis Human Breast Cancer; Cancer Res 2005: 65 (3); 907-912.

Philibert J C et al. Influence of Host Factors on Survival in Dogs with Malignant Mammary Gland Tumors; J Vet Intern Med 2003; 17:102-106.

Press M F et al. Expression of the Her2/neu proto-oncogene in normal human adult and fetal tissues; Oncogene, 5: 953-62.

Rungsipipat A et al.; C-erbB-2 oncogene and P21WAF/CIPI tumor suppressor gene expression as prognostic factors in canine mammary adenocarcinomas; Comp Clin Pathol 2008, 17:35-41.

Winston J et al. Immunohistochemical detection of Her=2/neu expression in spontaneous feline mammary tumours; Veterinary and Comparative Oncology 3, 1, 8-15, 2005.

Chang S Y et al. Enhanced efficacy of DNA vaccination against Her2/neu tumor antigen by genetic adjuvants; IJC vol 111 pages 86-95, 10 Aug. 2004

Pupa et al. HER2: A biomarker at the crossroads of breast cancer immunotherapy and molecular medicine. JCP Vol 205 pages 10-18, 10 May 2005.

Quaglino E et al. Concordant morphologic and gene expression data show that a vaccine halts HER2/neu preneoplastic lesions. JCI Vol 113 No 5 Mar. 2004

Bernhard H et al. Vaccination against the HER2/neu oncogenic protein. Endocrine-Related Cancer 9 (1) 33-44, 2002.

Berta, G N et al. Anti-HER2 DNA vaccine protects Syrian hamsters against squamous cell carcinomas. Br J Cancer, vol 93(11), 28 Nov. 2005.

Disis et al. Peptide-based, but not whole protein, vaccines elicit immunity to HER2/neu, an oncogenic self-protein. The Journal of Immunology 156: 3151-3158, May 1, 1996.

Eck et al. (Gene Based Therapy in The Pharmacological Basis of Therapeutics, Goodman and Gilman, Eds, 1996, pp. 77-101).

Zhai et al. Antigen-Specific Tumor Vaccines. The Journal of Immunology 156: 700-710, January 1996.

Verma and Somia. Gene and therapy-promises, problems and prospects. Nature 389: 239-242, September 1997.

Miller and Vile. Targeted vectors for gene therapy. FASEB J. 9: 190-199, 1995.

Deonarain, Mahendra. Ligand-targeted receptor-mediated vectors for gene delivery. Exp. Opin. Ther. Patents 8(1): 53-69, 1998.

Crystal. Transfer of Genes to Humans: Early Lessons and Obstacles to Success. Science 270: 404-410, Oct. 20, 1995.

B. Bouchard et al., "Induction of Pigmentation in Mouse Fibroblasts by Expression of Human Tyrosinase cDNA", J. Exp. Med., 1989, vol. 169, pp. 2029-2042.

B. Bouchard et al., "Production and Characterization of Antibodies against Human Tyrosinase", The Journal of Investigative Dermatology, 1994, vol. 102, No. 3, pp. 291-295.

J. Rowell et al., "Lysosome-Associated Membrane Protein-1-Mediated Targeting of the HIV-1 Envelope Protein to an Endosomal/Lysosomal Compartment Enhances Its Presentation to MHC Class II-Restricted T Cells", The American Association of Immunologists, 1995, pp. 1818-1828.

S. Krishnan et al., "Paving the way towards DNA vaccines", Nature Medicine, 1995, vol. 1, No. 6, pp. 521-522.

S. Barclay et al., "Rapid isolation of monoclonal antibodies specific for cell surface differentiation antigens", Proc. Natl. Acad. Sci. USA, 1986 vol. 83, pp. 4336-4340.

S. Vijayasaradhi et al., "Intracellular Sorting and Targeting of Melanosomal Membrane Proteins: Identification of Signals for Sorting of the Human Brown Locus Protein, GP75", The Journal of Cell Biology, 1995, vol. 130, No. 4, pp. 807-820.

D. Pardoll et al., "Exposing the Immunology of Naked DNA Vaccines", Immunity, Cell Press, 1995, vol. 3, pp. 165-169.

S. Vijayasaradhi et al., "The Melanoma Antigen gp75 is the Human Homologue of the Mouse b (Brown) Locus Gene Product", J. Exp. Med., 1990, vol. 171, pp. 1375-1380.

G. Adema et al., "Molecular Characterization of the Melanocyte Lineage-specific Antigen gp100", The Journal of Biology Chemistry, The American Society for Biochemistry and Molecular Biology, 1994, vol. 269, No. 31, pp. 20126-20133.

A. Houghton et al., "Recognition of Autoantigens by Patients with Melanoma", Annals New York Academy of Sciences, 1993, pp. 59-69.

C. Naftzger et al., "Immune response to a differentiation antigen induced by altered antigen: A study of tumor rejection and autoimmunity", Proc. Natl. Acad. Sci. USA, 1996, vol. 93, pp. 14809-14814.

F. Ausubel et al., "Expression of Proteins is Insect Cells using Baculoviral Vectors", Current Protocols in Molecular Biology, Greene Publishing and Wiley-Interscience, 1990, vol. 8, 16.8.1-16.11-7.

J. Ulmer et al., "Heterologous Protection Against Influenza by Injection of DNA Encoding a Viral Protein", Science, 1993, vol. 259, pp. 1745-1749.

C. Tiffs et al., "The Folding and Cell Surface Expression of CD4 Requires Glycosylation", The Journal of Biological Chemistry, 1992, vol. 267, No. 5, pp. 3268-3273.

S. Park, "JL1, A Novel Differentiation Antigen of Human Cortical Thymocyte", J. Exp. Med., The Rockefeller University Press, 1993, vol. 178, pp. 1447-1451.

C. Cabanas et al., "Characterization of a CD11c-Reactive Monoclonal Antibody (HCI/I) Obtained by Immunizing with Phorbol Ester Differentiated U937 Cells", Hybridoma, 1988, vol. 7, No. 2, pp. 167-177.

N. Nanda et al., "Induction of Anti-Self-Immunity to Cure Cancer", Cell, 1995, vol. 82, pp. 13-17. cited by other.

All of the above-mentioned applications, patents and references are herein incorporated in their entirety by reference.

SUMMARY OF THE INVENTION

It has now been found that the tolerance of the immune system for self-derived target differentiation antigens can be overcome and an immune response stimulated by administration of a xenogeneic differentiation antigen (wild-type or mutant) of the same type from a species different from the subject being treated (U.S. Pat. No. 6,328,969 & U.S. Pat. No. 7,556,805, to Sloan-Kettering, both incorporated by reference herein). For example, a rat differentiation antigen can be used to stimulate an immune response to the corresponding differentiation antigen in a canine subject. Administration of altered antigens in accordance with the invention results in an effective immunity against the original antigen expressed by the cancer in the treated subject. Thus, in accordance with a first aspect of the invention, there is provided a method for treating in a mammalian subject, comprising the step of administering to the subject an immunologically-effective amount of a xenogeneic mammary gland tumor-associated differentiation antigen.

Therapeutic differentiation antigens based on mammary gland carcinoma/tumor-associated differentiation antigens are used in accordance with the invention to treat, for example, mammary gland carcinoma post-surgical removal of tumors in subjects suffering from said cancers. In one embodiment of the invention, a plasmid comprising a sequence encoding a xenogeneic tyrosine kinase receptor, for example rat tyrosine kinase receptor, under the control of a suitable promoter, is administered to a subject. For example, dogs have been treated using plasmids comprising a DNA sequence encoding rat tyrosine kinase receptor with pronounced clinical benefit.

BRIEF DESCRIPTION OF THE DRAWINGS

FIG. 3 shows the nucleotide sequence for the pINGhuman-Tyrosinase plasmid, where the coding sequence for the human tyrosinase has been removed. This is the location into which the rat Her2/neu (nucleotides 17-3799 of SEQ ID NO:1) was inserted to produce the rHer2/neu-pING of the instant invention;

DETAILED DESCRIPTION OF THE INVENTION

Figure 1A:
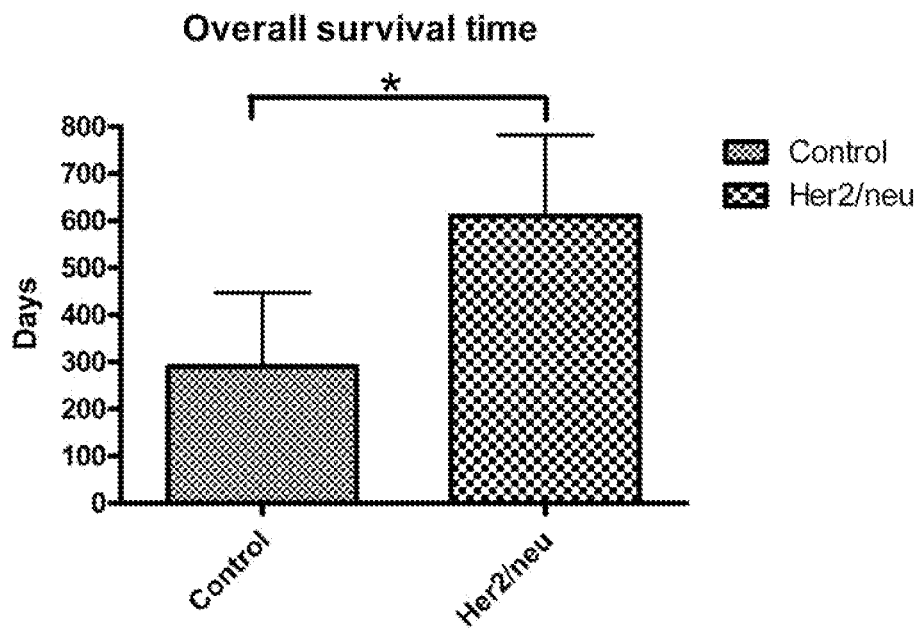
FIG. 1A shows overall survival time post-immunization and surgical resection of MGT.

The present invention provides a method for treating mammary gland tumors in a subject by stimulating an immune response to a mammary gland-associated differentiation antigen. The subject is preferably canine or feline, although the invention can be applied to other animal species, preferably mammalian or avian species, as well.

As used in the specification and claims of this application, the term "immune response" encompasses both cellular and humoral immune responses. Preferably, the immune response is sufficient to provide immunoprotection against growth of tumors expressing the target differentiation antigen. The term "stimulate" refers to the initial stimulation of a new immune response or to the enhancement of a pre-existing immune response.

In accordance with the invention, a subject is treated by administering a xenogeneic differentiation antigen of the same type as a target differentiation antigen expressed by mammary gland tumor cells of the subject in an amount effective to stimulate an immune response. Thus, for example, if the target differentiation antigen is the Her2/neu antigen found in mammary cells, the therapeutic antigen is a xenogeneic Her2/neu antigen.

In one embodiment, the inventive method may include the following steps: (1) immunization to an animal in need of a xenogeneic antigen, for example, the rat Her2/neu as set forth in SEQ ID NO:2 and encoded by nucleotides 106-3885 of the sequence as set forth in SEQ ID NO:1, (2) needle-free priming of immune responses, (3) electrotransfer-based booster, and (4) vaccination after tumor debulking by surgical primary therapy.

In another embodiment, the inventive method is carried out on subjects, including companion animals, without metastasis (i.e. in relatively early stages of mammary carcinoma disease progression).

In some embodiments, the boost comprises administering plasmids encoding xenogeneic antigens, for example those encoding rat Her2 protein (SEQ ID NO:2).

In some embodiments, the xenogeneic antigen is encoded by a nucleotide having favorable nucleotide substitutions with respect to the sequence as set forth in SEQ ID NO:1. Favorable substitutions include any changes that result in improved immune response against the Her2/neu expressed by the cells of the mammary tumor/carcinoma. Substitutions can include existing sequences, such as murine Her2 (SEQ ID NO:3), human Her2 (SEQ ID NO:4), or any other xenogeneic Her2 sequence, or fragment thereof, capable of eliciting a therapeutically effective immune response in a target animal against a Her2-associated mammary carcinoma.

In some embodiments, the boost comprises administering a xenogeneic differentiation antigen.

In other embodiments, the boost comprises administering a syngeneic differentiation antigen.

Xenogeneic differentiation antigen may be administered as a purified differentiation antigen derived from the source organism. Proteins can be purified for this purpose from cell lysates using column chromatography procedures. Proteins for this purpose may also be purified from recombinant sources, such as bacterial or yeast clones or mammalian or insect cell lines expressing the desired product.

Administration of the xenogeneic differentiation antigen can be accomplished by several routes. First, the xenogeneic differentiation antigen may be administered as part of a vaccine composition which may include one or more adjuvants such as alum, QS21, TITERMAX or its derivatives, incomplete or complete Freund's and related adjuvants, and cytokines such as granulocyte-macrophage colony stimulating factor, flt-3 ligand, interleukin-2, interleukin-4 and interleukin-12 for increasing the intensity of the immune response. The vaccine composition may be in the form of a xenogeneic differentiation antigen in a solution or a suspension, or the therapeutic differentiation antigen may be introduced in a lipid carrier such as a liposome. Such compositions will generally be administered by subcutaneous, intradermal or intramuscular route. Vaccine compositions containing expressed xenogeneic differentiation antigen are administered in amounts which are effective to stimulate an immune response to the target differentiation antigen in the subject. The preferred amount to be administered will depend on the species of the subject and on the specific antigen, but can be determined through routine preliminary tests in which increasing doses are given and the extent of antibody formation or T cell response is measured by ELISA or similar tests. T cell responses may also be measured by cellular immune assays, such as cytotoxicity, cytokine release assays and proliferation assays.

The xenogeneic differentiation antigen may also be introduced in accordance with the invention using a DNA immunization technique in which DNA encoding the antigen is introduced into the subject such that the xenogeneic differentiation antigen is expressed by the subject. cDNA encoding the differentiation antigen is combined with a promoter which is effective for expression of the nucleic acid polymer in mammalian cells. This can be accomplished by digesting the nucleic acid polymer with a restriction endonuclease and cloning into a plasmid containing a promoter such as the SV40 promoter, the cytomegalovirus (CMV) promoter or the Rous sarcoma virus (RSV) promoter. The resulting construct is then used as a vaccine for genetic immunization. The nucleic acid polymer could also be cloned into plasmid and viral vectors that are known to transduce mammalian cells. These vectors include retroviral vectors, adenovirus vectors, vaccinia virus vectors, pox virus vectors and adenovirus-associated vectors.

The nucleic acid constructs containing the promoter and the antigen-coding region can be administered directly or they can be packaged in liposomes or coated onto colloidal gold particles prior to administration. Techniques for packaging DNA vaccines into liposomes are known in the art, for example from Murray, ed. "Gene Transfer and Expression Protocols" Humana Pres, Clifton, N.J. (1991). Similarly, techniques for coating naked DNA onto gold particles are taught in Yang, "Gene transfer into mammalian somatic cells in vivo", Crit. Rev. Biotech. 12: 335-356 (1992), and techniques for expression of proteins using viral vectors are found in Adolph, K. ed. "Viral Genome Methods" CRC Press, Florida (1996).

For genetic immunization, the vaccine compositions are preferably administered intradermally, subcutaneously or intramuscularly by injection or by gas driven particle bombardment, and are delivered in an amount effective to stimulate an immune response in the host organism. The compositions may also be administered ex vivo to blood or bone marrow-derived cells (which include APCs) using liposomal transfection, particle bombardment or viral infection (including co-cultivation techniques). The treated cells are then reintroduced back into the subject to be immunized. While it will be understood that the amount of material needed will depend on the immunogenicity of each individual construct and cannot be predicted a priori, the process of determining the appropriate dosage for any given construct is straightforward. Specifically, a series of dosages of increasing size, starting at about 0.1 µg is administered and the resulting immune response is observed, for example by measuring antibody titer using an ELISA assay, detecting CTL response using a chromium release assay or detecting TH (helper T cell) response using a cytokine release assay.

Once tolerance is broken through the administration of the xenogeneic differentiation antigen, subsequent treatments with syngeneic differentiation may be employed to maintain and in some cases enhance the immune response. (See, Weber, et al., "Tumor immunity and autoimmunity induced by immunization with homologous DNA." J Clin Invest 102 (6):1258 (1998).) Thus, in one embodiment of the invention, the subject is first treated by administration of a xenogeneic differentiation antigen (for example for three treatment cycles), and subsequently by administration of a syngeneic differentiation antigen (for example for an additional three treatment cycles). As an alternative to treatment cycles using different therapeutic agents, one can use a single therapeutic agent containing both xenogeneic and syngeneic differentiation antigens. Thus, for example, a mixture of the rHer2-pING and hHer2-pING vectors, or a single vector encoding both rat and human Her2/neu under the control of a promoter such that they are expressed in a canine subject can be employed for the treatment of mammary gland tumor in canines. Vectors are available commercially, for example from Stratagene and other companies, which can express two independent genes. Commonly, these vectors use an internal ribosomal entry site, or IRES, between the two genes. This approach has the advantage of requiring approval for only a single therapeutic agent.

All documents cited herein are herein incorporated by reference in their entirety.

The invention will now be further described with reference to the following, non-limiting examples.

EXAMPLE 1

Her2/Neu Expression Plasmid Construction

Figure 2:
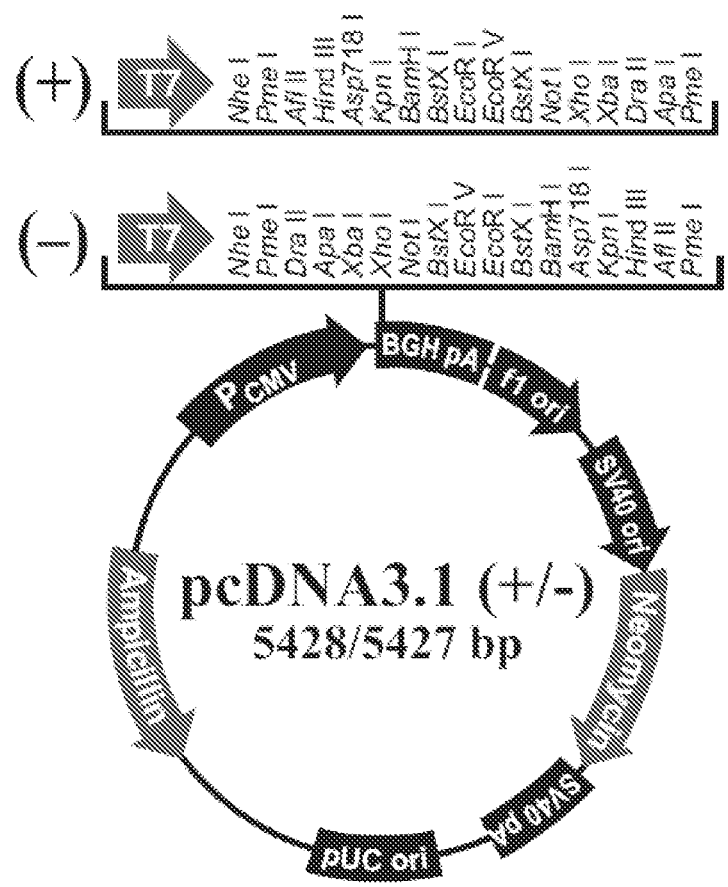
FIG. 2 shows a map of the pcDNA3.1 (+/−) plasmid.
Figure 4:
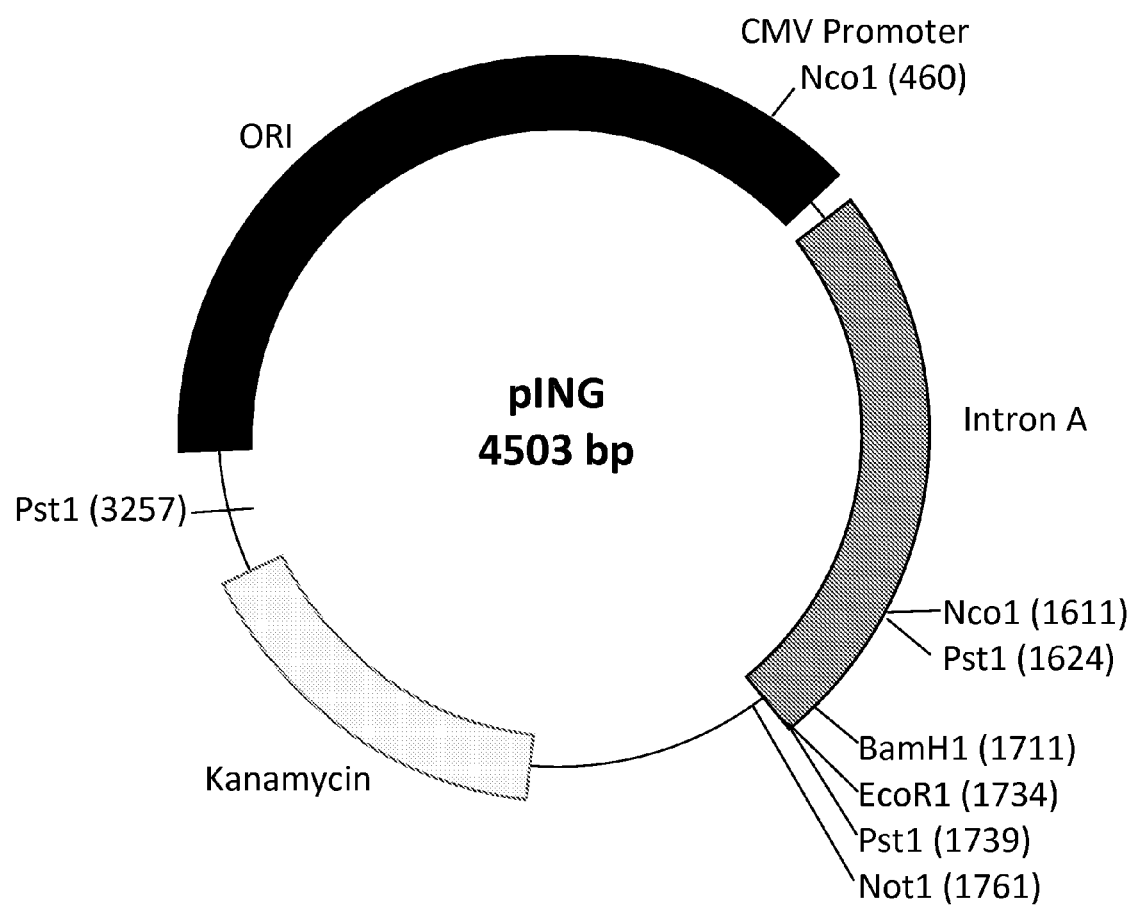
FIG. 4 shows a map of the pINGhumanTyrosinase plasmid.

The extracellular domain of rat HER2/neu (nucleotides 17-3799 of SEQ ID NO:1) was amplified by PCR from the pCMVneuNT (Amici et al., 1998) plasmid using the primers forward: 5'-CGAAGCTTACCATGGAGCTGGCGGC-CTGG-3' (SEQ ID NO:6) and reverse: 5'-CGGAATTCTTAT-GTCACCGGGCTGGC-3' (SEQ ID NO:7). The HindIII-EcoRI fragment was cloned into pcDNA3.1(+) (Invitrogen, Carlsbad, Calif.; and FIG. 2). The original sequence of the rat neu cDNA was described previously (Bargmann et al., 1986), and is herein set forth in SEQ ID NO:1, with the coding sequence from nucleotides 17 to 3799. The rat HER2/neu coding sequence was then subcloned into the pING vector (Bergman et al., Clin Cancer Res, 9: 1284-1290, 2003, backbone depicted in FIG. 3; map depicted in FIG. 3A; and sequence as set forth in SEQ ID NO:5), to yield rat HER2/neu-pING.

EXAMPLE 2

Immunization of Mammary Gland Tumor (MGT)-Positive Canines with pING-rHer2

In this trial, 10 dogs with MGT were enrolled and immunized with 100 µg of pING-rHer2 DNA per dose. The signalment for these dogs is set forth in Table 1 and the tumor staging is set forth in Table 2.

TABLE 1

Trial animal characteristics

|  | Age (yrs) | Breed | Weight (kg) |
| --- | --- | --- | --- |
| MGT 01 | 9 | Yorkshire Terrier | 1.75 |
| MGT 02 | 13 | Mixed | 9.8 |
| MGT 03 | 12 | Yorkshire Terrier | 5 |
| MGT 04 | 7 | Lhasa Apso | 11 |
| MGT 05 | 10 | Maltese | 3.35 |
| MGT 06 | 12 | Cavalier King Charles Spaniel | 9 |
| MGT 07 | 8 | Pomeranian | 2.8 |
| MGT08 | 12 | Maltese | 3.9 |
| MGT09 | 13 | Pomeranian | 2.7 |
| MGT10 | 12 | Yorkshire Terrier | 3 |
| Median | 12 | — | 3.6 |

TABLE 2

Tumor staging

|  | Tumor size (cm) | MGT Type | Stage |
| --- | --- | --- | --- |
| MGT 01 | 2 × 2 × 4<br>0.2 × 0.2 × 0.2<br>0.2 × 0.3 × 0.2<br>0.1 × 0.1 × 0.1<br>0.5 × 0.5 × 0.5<br>0.2 × 0.2 × 0.2<br>0.5 × 0.5 × 0.5 | Tubulopapillary carcinoma | $T_3N_0M_0$ |
| MGT 02 | 12 × 10 × 8<br>5 × 3 × 1.5<br>1 × 1 × 1<br>1 × 1 × 0.5<br>0.5 × 0.1 × 0.1 | Lipid rich carcinoma | $T_3N_0M_0$ |
| MGT 03 | 5.6 × 4.8 × 4.6<br>1.8 × 1.5 × 1.2 | Tubulopapillary carcinoma with fibroadenoma | $T_3N_0M_0$ |
| MGT 04 | 4.2 × 5.6 × 2.5 | Tubulopapillary carcinoma | $T_3N_0M_0$ |
| MGT 05 | 1.2 × 1 × 0.5<br>1 × 1.4 × 0.5<br>1 × 1 × 0.4<br>0.5 × 0.5 × 0.5 | Simple adenoma | $T_1N_0M_0$ |
| MGT 06 | 10 × 4 × 3 | Lipid rich carcinoma with fibroadenoma | $T_3N_0M_0$ |
| MGT 07 | 1 × 1 × 1<br>0.5 × 0.5 × 0.5 | Complex type | $T_1N_0M_0$ |
| MGT08 | 1 × 1 × 1<br>0.5 × 0.5 × 0.5 | Complex type | $T_1N_0M_0$ |
| MGT09 | 2.5 × 2 × 1<br>1.5 × 2 × 1 | Complex type | $T_1N_0M_0$ |
| MGT10 | 1 × 1 × 1<br>0.5 × 0.5 × 0.5<br>0.1 × 0.1 × 0.1 | Tubulopapillary carcinoma | $T_1N_0M_0$ |

As indicated, this group included five stage I and five stage III dogs, which all received three doses of vaccine at two week intervals. The first and second doses were administered with the VITAJET™ transdermal device and the third dose by intramuscular injection concurrent with electroporation. Vaccination was initiated following surgical removal of the MGT with concurrent ovariohysterectomy (OHE). All dogs were negative for regional lymph node and pulmonary metastasis. Disease free survival and overall survival times were calculated using day of surgery as day 0 with results presented in Table 3.

TABLE 3

Disease-free and overall survival time

| Dog | WHO Stage | Disease-free survival recurrence | Disease-free survival metastasis | Overall survival time (days) | Outcome |
|---|---|---|---|---|---|
| MGT 05 | I | 703 | 703 | 703 | alive |
| MGT 07 | I | 669 | 669 | 669 | alive |
| MGT 08 | I | 548 | 548 | 548 | alive |
| MGT 09 | I | 536 | 536 | 536 | alive |
| MGT 10 | I | 482 | 482 | 482 | dead |
| Stage I Dogs | | 548 | 548 | 548 | — |
| MGT 01 | III | 779 | 779 | 779 | alive |
| MGT 02 | III | 212 | 182 | 212 | dead |
| MGT 03 | III | 762 | 762 | 762 | alive |
| MGT 04 | III | 575 | 381 | 720 | alive w/met |
| MGT 06 | III | 686 | 686 | 686 | alive |
| Stage III Dogs | | 686 | 686 | 720 | — |
| All Dogs Median | | 622 | 609 | 678 | |

Figure 1B:
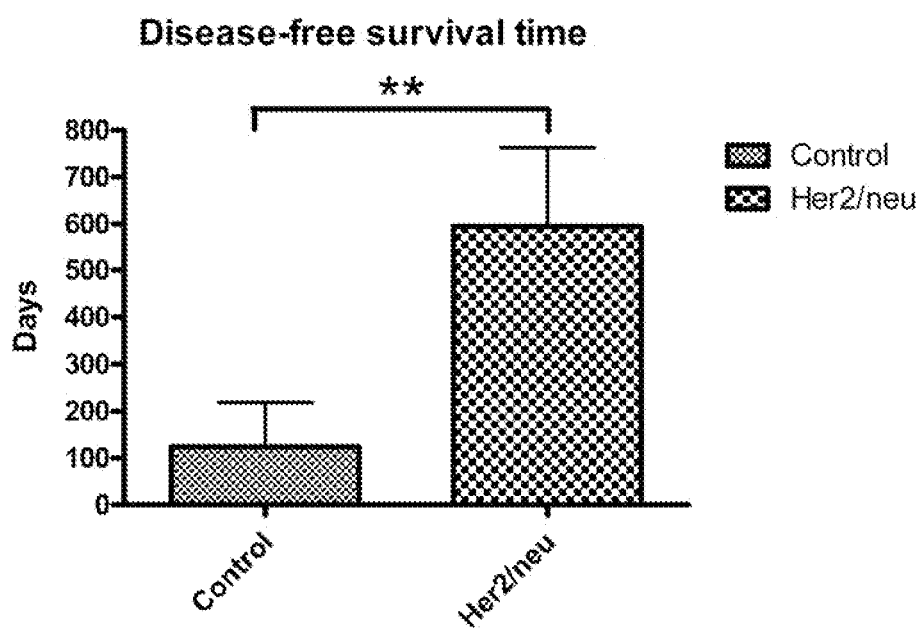
FIG. 1B shows disease-free survival time post-immunization and surgical resection of MGT.
Figure 1C:
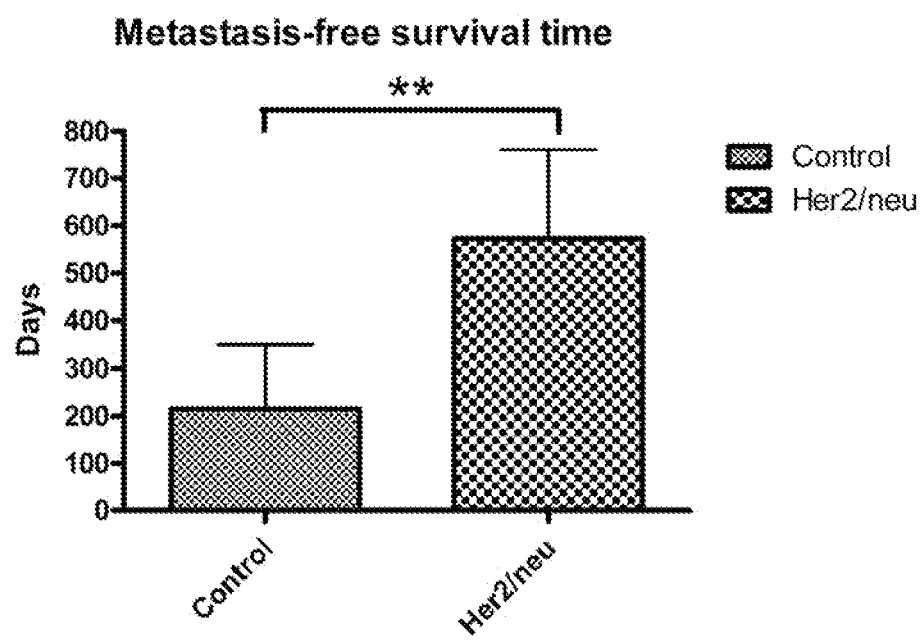
FIG. 1C shows metastasis-free survival time post-immunization and surgical resection of MGT.

A group of 19 dogs was identified as historical control cases. All control dogs underwent surgical removal of MGT with concurrent OHE and were negative for regional lymph node and pulmonary metastasis. This group included 7 stage I, 3 stage II, and 9 stage III dogs. Disease free and overall survival times were calculated for these dogs using day of surgery as day 0. The signalment for these dogs is set forth in Table 4 and tumor staging for each dog is set forth in Table 5. Disease free and overall survival times were calculated for the control group and are presented in FIGS. 1A-1C.

TABLE 4

Control dog signalment

| | Case Number | Age (yrs) | Breed | Weight (kg) |
|---|---|---|---|---|
| 1 | 9403460 | 7 | Mix | 1.75 |
| 2 | 9404023 | 14 | Poodle | 2.5 |
| 3 | 9405132 | 14 | Yorkshire | 2.3 |
| 4 | 9409179 | 12 | Finnish Spitz | 6.8 |
| 5 | 9409043 | 14 | Poodle | 3.2 |
| 6 | 9500057 | 9 | Lhasa Apso | 6.5 |
| 7 | 9500890 | 14 | Maltese | 6 |
| 8 | 9500959 | 15 | Cocker | 14 |
| 9 | 923543 | 11 | Siberian Huskies | 16 |
| 10 | 9405082 | 13 | Poodle | 3.9 |
| 11 | 9505202 | 9 | Mix | 12 |
| 12 | 9600998 | 10 | Maltese | 4.6 |
| 13 | 9700451 | 13 | Maltese | 2.7 |
| 14 | 892285 | 12 | Yorkshire | 1.6 |
| 15 | 9502927 | 14 | Maltese | 3.2 |
| 16 | 9405356 | 10 | Cocker | 12 |
| 17 | 9409104 | 11 | Maltese | 3.8 |
| 18 | 9503957 | 6 | Miniature Schnauzer | 4 |
| 19 | 9404023 | 14 | Poodle | 3 |
| | Median | 12 | | 3.9 |

TABLE 5

Tumor staging for control dogs

| Clinical NO. | Tumor size | MGT Type | Stage |
|---|---|---|---|
| 1 | 9403460 | 6 × 6 × 7 | Complex carcinoma | $T_3N_0M_0$ |
| 2 | 9404023 | 3 × 3 × 3 | Squamous cell carcinoma | $T_2N_0M_0$ |
| 3 | 9405132 | 7 × 4 × 7<br>2 × 2 × 2<br>0.3 × 0.2 × 0.2<br>0.5 × 0.5 × 0.5 | Simple or complex carcinoma | $T_3N_0M_0$ |
| 4 | 9409179 | 13 × 12 × 12<br>6 × 7 × 7<br>1 × 1 × 1 | Simple carcinoma with squamous cell carcinoma | $T_3N_0M_0$ |
| 5 | 9409043 | 3.5 × 2. × 1<br>3 × 1.5 × 1 | Tubulopapillary carcinoma | $T_2N_0M_0$ |
| 6 | 9500057 | 3 × 2 × 2<br>2 × 1 × 1 | Tubulopapillary carcinoma | $T_2N_0M_0$ |
| 7 | 9500890 | 8 × 3 × 1 | Simple carcinoma | $T_3N_0M_0$ |
| 8 | 9500959 | 8 × 3 × 2<br>2 × 1 × 0.5 | Adenocarcinoma | $T_3N_0M_0$ |
| 9 | 923543 | 5 × 5 × 4<br>0.2 × 0.2 × 0.2 | Simple carcinoma | $T_3N_0M_0$ |
| 10 | 9405082 | 5 × 4 × 3.5<br>3 × 3.5 × 3 | Simple carcinoma | $T_3N_0M_0$ |
| 11 | 9505202 | 0.3 × 0.3 × 0.3<br>1 × 1 × 0.5<br>0.4 × 0.4 × 0.4 | Tubulopapillary carcinoma | $T_1N_0M_0$ |
| 12 | 9600998 | 0.5 × 0.5 × 0.4<br>1 × 0.5 × 0.5 | Carcinoma | $T_1N_0M_0$ |
| 13 | 9700451 | 1 × 1 × 1<br>1 × 1 × 1 | Tubulopapillary carcinoma | $T_1N_0M_0$ |
| 14 | 892285 | 0.5 × 0.8 × 0.3<br>1 × 0.8 × 0.5 | Carcinoma in benign mixed tumor | $T_1N_0M_0$ |
| 15 | 9502927 | 5 × 4 × 4<br>0.5 × 0.5 × 0.5 | Carcinoma in benign mixed tumor | $T_3N_0M_0$ |
| 16 | 9405356 | 10 × 3 × 1.5 | Tubulopapillary carcinoma | $T_3N_0Mo$ |
| 17 | 9409104 | 1 × 1 × 1<br>0.5 × 0.5 × 0.5<br>2 × 2 × 2 | Adenocarcinoma | $T_1N_0M_0$ |
| 18 | 9503957 | 2 × 2 × 2<br>0.3 × 0.3 × 0.3 | Adenocarcinoma, complex type | $T_1N_0M_0$ |
| 19 | 9404023 | 2 × 2 × 1 | Adenocarcinoma, | $T_1N_0M_0$ |

Philibert et al. (2003) reviewed survival statistics for 97 dogs with MGT and reported median survival times for 41 dogs with MGT less than 3 cm in diameter to be 22 months (~666 days) versus 14 months (~424 days) for 56 dogs with MGT greater than 3 cm in diameter. In the absence of lymph node involvement or metastasis, tumor size less than 3 cm correlates with stage I disease and greater than 3 cm correlates with stage II or higher disease status. They did not find a difference in survival time for dogs in stages II, III or IV.

Overall median survival time for all dogs treated with the pING-rHer2 vaccine is 678 days. This was significantly higher as compared to the historical data from the 19 dogs provided by NTU indicating a median overall survival time of 300 days, and to the data published by Philibert et al. (2003) indicating 424 days overall survival time for dogs with stage II or greater MGT.

The pING-rHer2 DNA vaccine will target dogs and cats with tumors shown to over express the Her2 antigen based upon tumor tissue analysis using existing Her2 tissue expression assays. The vaccine will be administered using the Vet-jet™ transdermal device to deliver 100 μg of DNA into the medial thigh of dogs or lateral thigh of cats, at two week intervals for four doses. Dogs and cats that survive will receive a booster dose every six months.

The invention will now be described by the following non-limiting claims.

What is claimed is:

1. A method for treating canine mammary carcinoma/tumor in a dog suffering from a canine mammary carcinoma/tumor comprising mammary cells expressing a Her2/neu antigen, comprising:
   a) surgically debulking said tumor; and
   b) administering to said dog a clinically-effective amount of a first plasmid comprising a DNA sequence encoding a xenogeneic Her2/neu antigen under the control of a promoter which promotes expression of said Her2/neu antigen in said dog; and
   wherein canines receiving said plasmid exhibit significantly increased overall, disease-free, and/or metastasis-free survival times relative to canines receiving said surgical debulking without subsequent administration of said plasmid, thereby treating said carcinoma/tumor.

2. The method of claim 1, wherein said DNA sequence encoding a xenogeneic Her2/neu antigen comprises nucleotides 106-3885 of the sequence as set forth in SEQ ID NO:1.

3. The method of claim 1, further comprising administering via electrotransfer/electroporation a booster immunization, wherein said booster is either said first plasmid, or is a second plasmid capable of expressing in vivo in a canine a different xenogeneic Her2/neu, including those encoded by SEQ ID NOs:1, 3, or 4, or is a recombinant vector capable of expressing in vivo any Her2/neu protein, which is capable of eliciting a therapeutically effective immune response against heterologous Her2/neu expressed by said Her2/neu-associated carcinoma.

4. The method of claim 3 wherein:
   1) said first plasmid is administered without a needle;
   2) said first plasmid is capable of expressing in vivo in a canine a polypeptide comprising the sequence as set forth in SEQ ID NO:2; and/or
   3) said booster immunization comprises administering said first plasmid.

5. The method of claim 3 or 4, wherein said booster immunization is provided to surviving canines once every 3 to 6 months.

6. The method of claim 1, wherein said first plasmid is a non-viral plasmid.

7. The method of claim 1 performed concurrently with resection of a mammary gland tumor (MGT).

8. The method of claim 1, wherein said administration is performed using a needle-free delivery device.

9. The method of claim 3, wherein said booster immunization is provided at least once or at regular intervals.

10. The method of claim 1 or 8 wherein:
   a) mean overall survival time is at least 100 days greater in said canines receiving said plasmid relative to canines that do not receive said plasmid;
   b) mean disease-free survival time is at least 200 days greater in said canines receiving said plasmid relative to canines that do not receive said plasmid; and/or
   c) mean metastasis-free survival time is at least 200 days greater in said canines receiving said plasmid relative to canines that do not receive said plasmid.

11. The method of claim 10, wherein said three survival times are 100, 200, and 200 days greater in said canines receiving said plasmid relative to canines that do not receive said plasmid, respectively.

* * * * *

SEQUENCE LISTING

<160> NUMBER OF SEQ ID NOS: 4

<210> SEQ ID NO 1
<211> LENGTH: 4727
<212> TYPE: DNA
<213> ORGANISM: Rattus norvegicus

<400> SEQUENCE: 1

```
gcgccccttc ccaggcggcc ccttccggcg ccgcgcctgt gcctgccctc gccgcgcccc      60
gcgcccgcag cctggtccag cctgagccat ggggccggag ccgcaatgat catcatggag     120
ctggcggcct ggtgccgctg ggggttcctc ctcgccctcc tgccccccgg aatcgcgggc     180
acccaagtgt gtaccggcac agacatgaag ttgcggctcc ctgccagtcc tgagacccac     240
ctggacatgc tccgccacct gtaccagggc tgtcaggtag tgcagggcaa cttggagctt     300
acctacgtgc ctgccaatgc cagcctctca ttcctgcagg acatccagga agttcagggt     360
tacatgctca tcgctcacaa ccaggtgaag cgcgtcccac tgcaaaggct gcgcatcgtg     420
agagggaccc agctctttga ggacaagtat gccctggctg tgctagacaa ccgagatcct     480
caggacaatg tcgccgcctc cacccccagge agaaccccag aggggctgcg ggagctgcag     540
cttcgaagtc tcacagagat cctgaaggga ggagttttga tccgtgggaa ccctcagctc     600
tgctaccagg acatggtttt gtggaaggac gtcttccgca agaataacca actggctcct     660
gtcgatatag acaccaatcg ttcccgggcc tgtccacctt gtgccccccgc ctgcaaagac     720 aatcactgtt ggggtgagag tccggaagac tgtcagatct tgactggcac catctgtacc     780
agtggttgtg cccggtgcaa gggccggctg cccactgact gctgccatga gcagtgtgcc     840
gcaggctgca cgggccccaa gcattctgac tgcctggcct gcctccactt caatcatagt     900
ggtatctgtg agctgcactg cccagcccctc gtcacctaca acacagacac ctttgagtcc     960
atgcacaacc tgagggtcg ctacacctt ggtgccagct gcgtgaccac ctgcccctac    1020
aactacctgt ctacggaagt gggatcctgc actctggtgt gtccccccgaa taaccaagag    1080 gtcacagctg aggacggaac acagcgttgt gagaaatgca gcaagccctg tgctcgagtg    1140
tgctatggtc tgggcatgga gcaccttcga ggggcgaggg ccatcaccag tgacaatgtc    1200
caggagtttg atggctgcaa gaagatctttt gggagcctgg catttttgcc ggagagcttt    1260
gatggggacc cctcctccgg cattgctccg ctgaggcctg agcagctcca gtgttcgaa    1320 accctggagg agatcacagg ttacctgtac atctcagcat ggccagacag tctccgtgac    1380
ctcagtgtct tccagaacct tcgaatcatt cggggacgga ttctccacga tggcgcgtac    1440
tcattgacac tgcaaggcct ggggatccac tcgctgggc tgcgctcact gcgggagctg    1500
ggcagtggat tggctctgat tcaccgcaac gcccatctct gctttgtaca cactgtacct    1560
tgggaccagc tcttccggaa cccacatcag gccctgctcc acagtgggaa ccggccggaa    1620
gaggattgtg gtctcgaggg cttggtctgt aactcactgt gtgcccacgg gcactgctgg    1680
gggccagggc ccacccagtg tgtcaactgc agtcatttcc ttcggggcca ggagtgtgtg    1740
gaggagtgcc gagtatggaa ggggctcccc cgggagtatg tgagtgacaa gcgctgtctg    1800
ccgtgtcacc ccgagtgtca gcctcaaaac agctcagaga cctgctttgg atcggaggct    1860
gatcagtgtg cagcctgcgc ccactacaag gactcgtcct cctgtgtggc tcgctgcccc    1920
agtggtgtga accggaacct ctcctacatg cccatctgga agtacccgga tgaggagggc    1980
atatgccagc cgtgccccat caactgcacc cactcctgtg tggatctgga tgaacgaggc    2040
tgcccagcag agcagagagc cagcccggtg acattcatca ttgcaactgt agtgggcgtc    2100
```

```
ctgctgttcc tgatcttagt ggtggtcgtt ggaatcctaa tcaaacgaag gagacagaag    2160
atccggaagt atacgatgcg taggctgctg caggaaactg agttagtgga gccgctgacg    2220
cccagcggag caatgcccaa ccaggctcag atgcggatcc taaaagagac ggagctaagg    2280
aaggtgaagg tgcttggatc aggagctttt ggcactgtct acaagggcat ctggatccca    2340
gatggggaga atgtgaaaat ccccgtggct atcaaggtgt tgagagaaaa cacatctcct    2400
aaagccaaca agaaaattct agatgaagcg tatgtgatgg ctggtgtggg ttctccgtat    2460
gtgtcccgcc tcctgggcat ctgcctgaca tccacagtac agctggtgac acagcttatg    2520
ccctacggct gccttctgga ccatgtccga gaacaccgag gtcgcctagg ctcccaggac    2580
ctgctcaact ggtgtgttca gattgccaag gggatgagct acctggagga cgtgcggctt    2640
gtacacaggg acctggctgc ccggaatgtg ctagtcaaga gtcccaacca cgtcaagatt    2700
acagatttcg ggctggctcg gctgctggac attgatgaga cagagtacca tgcagatggg    2760
ggcaaggtgc ccatcaaatg gatggcattg gaatctattc tcagacgccg gttcacccat    2820
cagagtgatg tgtggagcta tggagtgact gtgtgggagc tgatgacttt tggggccaaa    2880
ccttacgatg gaatcccagc ccgggagatc cctgatttgc tggagaaggg agaacgccta    2940
cctcagcctc aatctgcac cattgatgtc tacatgatta tggtcaaatg ttggatgatt    3000
gactctgaat gtcgcccgag attccgggag ttggtgtcag aattttcacg tatggcgagg    3060
gacccccagc gttttgtggt catccagaac gaggacttgg gcccatccag ccccatggac    3120
agtaccttct accgttcact gctggaagat gatgacatgg gtgacctggt agacgctgaa    3180
gagtatctgg tgcccagca gggattcttc tccccggacc ctaccccagg cactgggagc    3240
acagcccata gaaggcaccg cagctcgtcc accaggagtg gaggtggtga gctgacactg    3300
ggcctggagc cctcggaaga agggcccccc agatctccac tggctccctc ggaagggggct    3360 ggctccgatg tgtttgatgg tgacctggca atgggggtaa ccaaagggct gcagagcctc    3420
tctccacatg acctcagccc tctacagcgg tacagcgagg accccacatt acctctgccc    3480
cccgagactg atggctatgt tgctcccctg gcctgcagcc ccagcccga gtatgtgaac    3540 caatcagagg ttcagcctca gcctcctta accccagagg gtcctctgcc tcctgtccgg    3600
cctgctggtg ctactctaga aagacccaag actctctctc ctgggaagaa tggggttgtc    3660
aaagacgttt ttgccttcgg gggtgctgtg gagaaccctg aatacttagt accgagagaa    3720
ggcactgcct ctccgcccca cccttctcct gccttcagcc cagcctttga caacctctat    3780
tactgggacc agaactcatc ggagcagggg cctccaccaa gtaactttga agggaccccc    3840
actgcagaga accctgagta cctaggcctg gatgtacctg tatgagacgt gtgcagacgt    3900
cctgtgcttt cagagtgggg aaggcctgac ttgtggtctc catcgccaca agcagggag    3960 agggtcctct ggccacatta catccagggc agacggctct accaggaacc tgccccgagg    4020
aacctttcct gctgcttga atcctgagtg gttaagaggg ccctgcctgg ctgggagaga    4080
tggcactgga cggcctctgg attacagacc ctgccctgac agactatagg gtccagtggg    4140
tatcatggcc atggcttctt gcctggcctg gctctcttgg ttctgaggac tgaggaaagc    4200
tcagcctaga agggaagagg tctggaggga acatcctggg aacaggacaa gcccactagga    4260 ctgagacaca tgcatcccaa caggggctg cactttcatc cagaccagtc tttgtacaga    4320
gtgtattttg ttctgttttt acttttgctt ttttttttaa aaaagatga aataaggaca    4380 cggagggaga gtgatgttta gggaatggtg tccctctttc ttcatttaca atgagatttg    4440
taaaatagct gggccccagc ctatgcctgg gagtggtccc aggctagacc ttactgctca    4500
```

-continued

```
cctgacacac agctcctcct tgagttgagt gtgtagaagt tttccaaaag tttgagatgg    4560
tttggctttg gggttgaggg actgggaagt taggatcctt tctgagggcc ctttggcaac    4620
aggatcattc ttcattggac gcactcattc caaggctacc cctagaatga agtccttccc    4680
tcccagtggg agagtggccc ttgaaaggag cactgtcaca tgactca                  4727
```

<210> SEQ ID NO 2
<211> LENGTH: 1259
<212> TYPE: PRT
<213> ORGANISM: Rattus norvegicus

<400> SEQUENCE: 2

```
Met Ile Ile Met Glu Leu Ala Ala Trp Cys Arg Trp Gly Phe Leu Leu
1               5                   10                  15

Ala Leu Leu Pro Pro Gly Ile Ala Gly Thr Gln Val Cys Thr Gly Thr
            20                  25                  30

Asp Met Lys Leu Arg Leu Pro Ala Ser Pro Glu Thr His Leu Asp Met
        35                  40                  45

Leu Arg His Leu Tyr Gln Gly Cys Gln Val Val Gln Gly Asn Leu Glu
    50                  55                  60

Leu Thr Tyr Val Pro Ala Asn Ala Ser Leu Ser Phe Leu Gln Asp Ile
65                  70                  75                  80

Gln Glu Val Gln Gly Tyr Met Leu Ile Ala His Asn Gln Val Lys Arg
                85                  90                  95

Val Pro Leu Gln Arg Leu Arg Ile Val Arg Gly Thr Gln Leu Phe Glu
            100                 105                 110

Asp Lys Tyr Ala Leu Ala Val Leu Asp Asn Arg Asp Pro Gln Asp Asn
        115                 120                 125

Val Ala Ala Ser Thr Pro Gly Arg Thr Pro Glu Gly Leu Arg Glu Leu
    130                 135                 140

Gln Leu Arg Ser Leu Thr Glu Ile Leu Lys Gly Gly Val Leu Ile Arg
145                 150                 155                 160

Gly Asn Pro Gln Leu Cys Tyr Gln Asp Met Val Leu Trp Lys Asp Val
                165                 170                 175

Phe Arg Lys Asn Asn Gln Leu Ala Pro Val Asp Ile Asp Thr Asn Arg
            180                 185                 190

Ser Arg Ala Cys Pro Pro Cys Ala Pro Ala Cys Lys Asp Asn His Cys
        195                 200                 205

Trp Gly Glu Ser Pro Glu Asp Cys Gln Ile Leu Thr Gly Thr Ile Cys
    210                 215                 220

Thr Ser Gly Cys Ala Arg Cys Lys Gly Arg Leu Pro Thr Asp Cys Cys
225                 230                 235                 240

His Glu Gln Cys Ala Ala Gly Cys Thr Gly Pro Lys His Ser Asp Cys
                245                 250                 255

Leu Ala Cys Leu His Phe Asn His Ser Gly Ile Cys Glu Leu His Cys
            260                 265                 270

Pro Ala Leu Val Thr Tyr Asn Thr Asp Thr Phe Glu Ser Met His Asn
        275                 280                 285

Pro Glu Gly Arg Tyr Thr Phe Gly Ala Ser Cys Val Thr Thr Cys Pro
    290                 295                 300

Tyr Asn Tyr Leu Ser Thr Glu Val Gly Ser Cys Thr Leu Val Cys Pro
305                 310                 315                 320

Pro Asn Asn Gln Glu Val Thr Ala Glu Asp Gly Thr Gln Arg Cys Glu
                325                 330                 335
```

```
Lys Cys Ser Lys Pro Cys Ala Arg Val Cys Tyr Gly Leu Gly Met Glu
            340                 345                 350

His Leu Arg Gly Ala Arg Ala Ile Thr Ser Asp Asn Val Gln Glu Phe
            355                 360                 365

Asp Gly Cys Lys Lys Ile Phe Gly Ser Leu Ala Phe Leu Pro Glu Ser
            370                 375             380

Phe Asp Gly Asp Pro Ser Ser Gly Ile Ala Pro Leu Arg Pro Glu Gln
385                 390                 395                 400

Leu Gln Val Phe Glu Thr Leu Glu Glu Ile Thr Gly Tyr Leu Tyr Ile
                405                 410                 415

Ser Ala Trp Pro Asp Ser Leu Arg Asp Leu Ser Val Phe Gln Asn Leu
            420                 425                 430

Arg Ile Ile Arg Gly Arg Ile Leu His Asp Gly Ala Tyr Ser Leu Thr
            435                 440                 445

Leu Gln Gly Leu Gly Ile His Ser Leu Gly Leu Arg Ser Leu Arg Glu
            450                 455                 460

Leu Gly Ser Gly Leu Ala Leu Ile His Arg Asn Ala His Leu Cys Phe
465                 470                 475                 480

Val His Thr Val Pro Trp Asp Gln Leu Phe Arg Asn Pro His Gln Ala
                485                 490                 495

Leu Leu His Ser Gly Asn Arg Pro Glu Glu Asp Cys Gly Leu Glu Gly
            500                 505                 510

Leu Val Cys Asn Ser Leu Cys Ala His Gly His Cys Trp Gly Pro Gly
            515                 520                 525

Pro Thr Gln Cys Val Asn Cys Ser His Phe Leu Arg Gly Gln Glu Cys
            530                 535                 540

Val Glu Glu Cys Arg Val Trp Lys Gly Leu Pro Arg Glu Tyr Val Ser
545                 550                 555                 560

Asp Lys Arg Cys Leu Pro Cys His Pro Glu Cys Gln Pro Gln Asn Ser
            565                 570                 575

Ser Glu Thr Cys Phe Gly Ser Glu Ala Asp Gln Cys Ala Ala Cys Ala
            580                 585                 590

His Tyr Lys Asp Ser Ser Ser Cys Val Ala Arg Cys Pro Ser Gly Val
            595                 600                 605

Lys Pro Asp Leu Ser Tyr Met Pro Ile Trp Lys Tyr Pro Asp Glu Glu
            610                 615                 620

Gly Ile Cys Gln Pro Cys Pro Ile Asn Cys Thr His Ser Cys Val Asp
625                 630                 635                 640

Leu Asp Glu Arg Gly Cys Pro Ala Glu Gln Arg Ala Ser Pro Val Thr
                645                 650                 655

Phe Ile Ile Ala Thr Val Val Gly Val Leu Leu Phe Leu Ile Leu Val
            660                 665                 670

Val Val Val Gly Ile Leu Ile Lys Arg Arg Arg Gln Lys Ile Arg Lys
            675                 680                 685

Tyr Thr Met Arg Arg Leu Leu Gln Glu Thr Glu Leu Val Glu Pro Leu
            690                 695                 700

Thr Pro Ser Gly Ala Met Pro Asn Gln Ala Gln Met Arg Ile Leu Lys
705                 710                 715                 720

Glu Thr Glu Leu Arg Lys Val Lys Val Leu Gly Ser Gly Ala Phe Gly
                725                 730                 735

Thr Val Tyr Lys Gly Ile Trp Ile Pro Asp Gly Glu Asn Val Lys Ile
            740                 745                 750
```

```
Pro Val Ala Ile Lys Val Leu Arg Glu Asn Thr Ser Pro Lys Ala Asn
        755                 760                 765

Lys Glu Ile Leu Asp Glu Ala Tyr Val Met Ala Gly Val Gly Ser Pro
    770                 775                 780

Tyr Val Ser Arg Leu Leu Gly Ile Cys Leu Thr Ser Thr Val Gln Leu
785                 790                 795                 800

Val Thr Gln Leu Met Pro Tyr Gly Cys Leu Leu Asp His Val Arg Glu
                805                 810                 815

His Arg Gly Arg Leu Gly Ser Gln Asp Leu Leu Asn Trp Cys Val Gln
            820                 825                 830

Ile Ala Lys Gly Met Ser Tyr Leu Glu Asp Val Arg Leu Val His Arg
        835                 840                 845

Asp Leu Ala Ala Arg Asn Val Leu Val Lys Ser Pro Asn His Val Lys
    850                 855                 860

Ile Thr Asp Phe Gly Leu Ala Arg Leu Leu Asp Ile Asp Glu Thr Glu
865                 870                 875                 880

Tyr His Ala Asp Gly Gly Lys Val Pro Ile Lys Trp Met Ala Leu Glu
                885                 890                 895

Ser Ile Leu Arg Arg Arg Phe Thr His Gln Ser Asp Val Trp Ser Tyr
            900                 905                 910

Gly Val Thr Val Trp Glu Leu Met Thr Phe Gly Ala Lys Pro Tyr Asp
        915                 920                 925

Gly Ile Pro Ala Arg Glu Ile Pro Asp Leu Leu Glu Lys Gly Glu Arg
    930                 935                 940

Leu Pro Gln Pro Pro Ile Cys Thr Ile Asp Val Tyr Met Ile Met Val
945                 950                 955                 960

Lys Cys Trp Met Ile Asp Ser Glu Cys Arg Pro Arg Phe Arg Glu Leu
                965                 970                 975

Val Ser Glu Phe Ser Arg Met Ala Arg Asp Pro Gln Arg Phe Val Val
            980                 985                 990

Ile Gln Asn Glu Asp Leu Gly Pro  Ser Ser Pro Met Asp  Ser Thr Phe
        995                 1000                 1005

Tyr Arg  Ser Leu Leu Glu Asp  Asp Asp Met Gly Asp  Leu Val Asp
    1010                 1015                 1020

Ala Glu  Glu Tyr Leu Val Pro  Gln Gln Gly Phe Phe  Ser Pro Asp
    1025                 1030                 1035

Pro Thr  Pro Gly Thr Gly Ser  Thr Ala His Arg Arg  His Arg Ser
    1040                 1045                 1050

Ser Ser  Thr Arg Ser Gly Gly  Gly Glu Leu Thr Leu  Gly Leu Glu
    1055                 1060                 1065

Pro Ser  Glu Glu Gly Pro Pro  Arg Ser Pro Leu Ala  Pro Ser Glu
    1070                 1075                 1080

Gly Ala  Gly Ser Asp Val Phe  Asp Gly Asp Leu Ala  Met Gly Val
    1085                 1090                 1095

Thr Lys  Gly Leu Gln Ser Leu  Ser Pro His Asp Leu  Ser Pro Leu
    1100                 1105                 1110

Gln Arg  Tyr Ser Glu Asp Pro  Thr Leu Pro Leu Pro  Pro Glu Thr
    1115                 1120                 1125

Asp Gly  Tyr Val Ala Pro Leu  Ala Cys Ser Pro Gln  Pro Glu Tyr
    1130                 1135                 1140

Val Asn  Gln Ser Glu Val Gln  Pro Gln Pro Pro Leu  Thr Pro Glu
    1145                 1150                 1155
```

```
Gly Pro Leu Pro Pro Val Arg Pro Ala Gly Ala Thr Leu Glu Arg
    1160            1165                1170
Pro Lys Thr Leu Ser Pro Gly Lys Asn Gly Val Val Lys Asp Val
1175                1180                1185
Phe Ala Phe Gly Gly Ala Val Glu Asn Pro Glu Tyr Leu Val Pro
    1190                1195                1200
Arg Glu Gly Thr Ala Ser Pro Pro His Pro Ser Pro Ala Phe Ser
1205                1210                1215
Pro Ala Phe Asp Asn Leu Tyr Tyr Trp Asp Gln Asn Ser Ser Glu
    1220                1225                1230
Gln Gly Pro Pro Pro Ser Asn Phe Glu Gly Thr Pro Thr Ala Glu
1235                1240                1245
Asn Pro Glu Tyr Leu Gly Leu Asp Val Pro Val
    1250                1255

<210> SEQ ID NO 3
<211> LENGTH: 3768
<212> TYPE: DNA
<213> ORGANISM: Mus musculus

<400> SEQUENCE: 3
```

| | | | | | |
|---|---|---|---|---|---|
| atggagctgg | cggcctggtg | ccgttggggg | ttcctcctcg | ccctcctgtc | cccggagcc | 60 |
| gcgggtaccc | aagtgtgtac | cggtaccgac | atgaagttgc | gactccctgc | cagtcctgag | 120 |
| acccacctgg | acatgcttcg | ccacctctac | cagggctgtc | aggtggtgca | gggcaatttg | 180 |
| gagcttacct | acctgcccgc | caatgccagc | ctctcattcc | tgcaggacat | ccaggaagtc | 240 |
| cagggataca | tgctcatcgc | tcacaaccga | gtgaaacacg | tcccactgca | gaggttgcgc | 300 |
| atcgtgagag | ggactcagct | cttcgaggac | aagtatgccc | tggctgtgct | agacaaccga | 360 |
| gacccttttgg | acaacgtcac | caccgccgcc | ccaggcagaa | cccagaagg | gctgcgggag | 420 |
| ctgcagcttc | gaagtctcac | agagatcttg | aagggaggag | ttttgatccg | tgggaaccct | 480 |
| cagctctgct | accaggacat | ggttttgtgg | aaggatgtcc | tccgtaagaa | taaccagctg | 540 |
| gctcctgtcg | acatggacac | caatcgttcc | cgggcctgtc | caccttgtgc | cccaacctgc | 600 |
| aaagacaatc | actgttgggg | tgagagtcct | gaagactgtc | agatcttgac | tggcaccatc | 660 |
| tgtactagtg | gctgtgcccg | tgcaagggc | cggctgccca | ctgactgttg | ccatgagcag | 720 |
| tgtgctgcag | gctgcacggg | tcccaagcat | tctgactgcc | tggcctgcct | ccacttcaat | 780 |
| catagtggta | tctgtgagct | gcactgcccg | ccctcatca | cctacaacac | agacaccttc | 840 |
| gagtccatgc | tcaaccctga | gggtcgctac | acctttggtg | ccagctgtgt | gaccacctgc | 900 |
| ccctacaact | acctctccac | ggaagtggga | tcctgcactc | tggtctgtcc | ccgaacaac | 960 |
| caagaggtca | cagctgagga | cggaacacag | cggtgtgaga | aatgcagcaa | gcctgtgct | 1020 |
| ggagtatgct | atggtctggg | catggagcac | ctccgagggg | cgagggccat | caccagtgac | 1080 |
| aatatccagg | agtttgctgg | ctgcaagaag | atctttggga | gcctggcatt | tttgccggag | 1140 |
| agctttgatg | ggaaccctc | ctccggcgtt | gccccactga | agccagagca | tctccaagtg | 1200 |
| ttcgaaaccc | tggaggagat | cacaggttac | ctatacattt | cagcatggcc | agagagcttc | 1260 |
| caagacctca | gtgtcttcca | gaaccttcgg | gtcattcggg | gacggattct | ccatgatggt | 1320 |
| gcttactcat | tgacgttgca | aggcctgggg | attcactcac | tggggctacg | ctcactgcgg | 1380 |
| gagctgggca | gtggattggc | tctcattcac | cgcaacaccc | atctctgctt | tgtaaacact | 1440 |
| gtaccttggg | accagctctt | ccggaacccg | caccaggccc | tactccacag | tgggaaccgg | 1500 |

```
ccagaagagg catgtggtct tgagggcttg gtctgtaact cactgtgtgc ccgtgggcac    1560
tgctgggggc cagggcccac ccagtgtgtc aactgcagtc agttcctccg gggccaggag    1620
tgtgtggagg agtgccgagt atggaagggg ctccccaggg agtatgtgag gggcaagcac    1680
tgtctgccat gccaccccga gtgtcagcct caaaacagct cggagacctg ctatggatcg    1740
gaggctgacc agtgtgaggc ttgtgcccac tacaaggact catcttcctg tgtggctcgc    1800
tgccccagtg gtgtgaagcc agacctctcc tacatgccta tctggaagta cccggatgag    1860
gagggcatat gtcagccatg ccccatcaac tgcacccact catgtgtgga cctggacgaa    1920
cgaggctgcc cagcagagca gagagccagc ccagtgacat tcatcattgc aactgtggtg    1980
ggcgtcctgt tgttcctgat catagtggtg gtcattggaa tcctaatcaa acgaaggcga    2040
cagaagatcc ggaagtatac catgcgtagg ctgctgcagg agaccgagct ggtggagccg    2100
ctgacgccca gtggagctgt gcccaaccag gctcagatgc ggatcctaaa ggagacagag    2160
ctaaggaagc tgaaggtgct tgggtcagga gccttcggca ctgtctacaa gggcatctgg    2220
atcccagatg gggagaacgt gaaaatcccc gtggccatca aggtgttgag ggaaaacaca    2280
tctcctaaag ctaacaaaga aatcctagat gaagcgtacg tcatggctgg tgtgggttct    2340
ccatatgtgt cccgcctcct gggcatctgc ctgacatcca cagtgcagct ggtgacacag    2400
cttatgccct atggctgcct tctggaccat gtccgagaac accgaggtcg cttaggctcc    2460
caggacctgc tcaactggtg tgttcagatt gccaagggga tgagctacct ggaggaagtt    2520
cggcttgttc acagggacct agctgcccga aacgtgctag tcaagagtcc caaccacgtc    2580
aagattaccg acttcgggct ggcacggctg ctggacattg atgagactga ataccatgca    2640
gatgggggca aggtgcccat caagtggatg gcattggaat ctattctcag acgccggttc    2700
acccatcaga gtgatgtgtg gagctatggt gtgactgtgt gggagctgat gacctttggg    2760
gccaaacctt acgatgggat cccagctcgg gagatccctg atttgctgga agggagaa    2820 cgcctacctc agcctccaat ctgcaccatc gacgtctaca tgatcatggt caaatgttgg    2880
atgattgact ccgaatgtcg cccgagattc cgggagttgg tatcagaatt ctcccgtatg    2940
gcaagggacc cccagcgctt tgtggtcatc cagaacgagg acttaggccc ctccagcccc    3000
atggacagca ccttctaccg ttcactgctg gaggatgatg acatggggga gctggtcgat    3060
gctgaagagt acctggtacc ccagcaggga ttcttctccc cagaccctgc cctaggtact    3120
gggagcacag cccaccgcag acaccgcagc tcgtcggcca ggagtggcgg tggtgagctg    3180
acactgggcc tggagccctc ggaagaagag ccccccagat ctccactggc tccctccgaa    3240
ggggctggct ccgatgtgtt tgatggtgac ctggcagtgg gggtaaccaa aggactgcag    3300
agcctctctc cacatgacct cagccctcta cagcggtaca gtgaggatcc cacattacct    3360 ctgcccccg agactgatgg ctacgttgct cccctggcct gcagccccca gcccgagtat    3420
gtgaaccagc cagaggttcg gcctcagtct cccttgaccc cagagggtcc tccgcctccc    3480
atccgacctg ctggtgctac tctagaaaga cccaagactc tctctcctgg gaaaaatggg    3540
gttgtcaaag acgttttgc ctttgggggt gctgtggaga accctgaata cttagcaccc    3600
agagcaggca ctgcctctca gccccaccct tctcctgcct tcagcccagc ctttgacaac    3660
ctctattact gggaccagaa ctcatcggag cagggtcctc caccaagtac ctttgaaggg    3720 accccccactg cagagaaccc tgagtaccta ggcctggatg tgccagta              3768
```

-continued

```
<210> SEQ ID NO 4
<211> LENGTH: 3765
<212> TYPE: DNA
<213> ORGANISM: homo sapiens

<400> SEQUENCE: 4
atggagctgg cggccttgtg ccgctggggg ctcctcctcg ccctcttgcc ccccggagcc      60
gcgagcaccc aagtgtgcac cggcacagac atgaagctgc ggctccctgc cagtcccgag     120
acccacctgg acatgctccg ccacctctac cagggctgcc aggtggtgca gggaaacctg     180
gaactcacct acctgcccac caatgccagc ctgtccttcc tgcaggatat ccaggaggtg     240
cagggctacg tgctcatcgc tcacaaccaa gtgaggcagg tcccactgca gaggctgcgg     300
attgtgcgag gcacccagct cttTgaggac aactatgccc tggccgtgct agacaatgga     360
gacccgctga caataccac ccctgtcaca ggggcctccc caggaggcct gcgggagctg     420
cagcttcgaa gcctcacaga gatcttgaaa ggaggggtct tgatccagcg gaaccccag     480 ctctgctacc aggacacgat tttgtggaag gacatcttcc acaagaacaa ccagctggct     540
ctcacactga tagacaccaa ccgctctcgg gcctgccacc cctgttctcc gatgtgtaag     600
ggctcccgct gctggggaga gagttctgag gattgtcaga gcctgacgcg cactgtctgt     660
gccggtggct gtgcccgctg caaggggcca ctgcccactg actgctgcca tgagcagtgt     720
gctgccggct gcacgggccc caagcactct gactgcctgg cctgcctcca cttcaaccac     780
agtggcatct gtgagctgca ctgcccagcc ctggtcacct acaacacaga cacgtttgag     840
tccatgccca tcccgaggg ccggtataca ttcggcgcca gctgtgtgac tgcctgtccc     900
tacaactacc tttctacgga cgtgggatcc tgcacctcg tctgccccct gcacaaccaa     960
gaggtgacag cagaggatgg aacacagcgg tgtgagaagt gcagcaagcc ctgtgcccga    1020
gtgtgctatg gtctgggcat ggagcacttg cgagaggtga gggcagttac cagtgccaat    1080
atccaggagt ttgctggctg caagaagatc tttgggagcc tggcatttct gccggagagc    1140
tttgatgggg acccagcctc caacactgcc ccgctccagc cagagcagct ccaagtgttt    1200
gagactctgg aagagatcac aggttaccta tacatctcag catggccgga cagcctgcct    1260
gacctcagcg tcttccagaa cctgcaagta atccggggac gaattctgca caatggcgcc    1320
tactcgctga cccctgcaagg gctgggcatc agctggctgg ggctgcgctc actgagggaa    1380
ctgggcagtg gactggccct catccaccat aacacccacc tctgcttcgt gcacacggtg    1440
ccctgggacc agctctttcg gaacccgcac caagctctgc tccacactgc caaccggcca    1500
gaggacgagt gtgtgggcga gggcctggcc tgccaccagc tgtgcgcccg agggcactgc    1560
tggggtccag gcccacccca gtgtgtcaac tgcagccagt tccttcgggg ccaggagtgc    1620
gtggaggaat gccgagtact gcaggggctc ccCaggagt atgtgaatgc caggcactgt    1680
ttgccgtgcc accctgagtg tcagccccag aatggctcag tgacctgttt tggaccggag    1740
gctgaccagt gtgtggcctg tgcccactat aaggacccTc ccttctgcgt ggcccgctgc    1800
cccagcggtg tgaaacctga cctctcctac atgcccatct ggaagtttcc agatgaggag    1860
ggcgcatgcc agccttgccc catcaactgc acccactcct gtgtggacct ggatgacaag    1920
ggctgccccg ccgagcagag agccagccct ctgacgtcca tcatctctgc ggtggttggc    1980
attctgctgg tcgtggtctt gggggtggtc tttgggatcc tcatcaagcg acggcagcag    2040
aagatccgga agtacacgat gcggagactg ctgcaggaaa cggagctggt ggagccgctg    2100
acacctagcg gagcgatgcc caaccaggcg cagatgcgga tcctgaaaga gacggagctg    2160
```

-continued

```
aggaaggtga aggtgcttgg atctggcgct tttggcacag tctacaaggg catctggatc    2220
cctgatgggg agaatgtgaa aattccagtg gccatcaaag tgttgaggga aaacacatcc    2280
cccaaagcca acaaagaaat cttagacgaa gcatacgtga tggctggtgt gggctcccca    2340
tatgtctccc gccttctggg catctgcctg acatccacgg tgcagctggt gacacagctt    2400
atgccctatg gctgcctctt agaccatgtc cgggaaaacc gcggacgcct gggctcccag    2460
gacctgctga actggtgtat gcagattgcc aaggggatga gctacctgga ggatgtgcgg    2520
ctcgtacaca gggacttggc cgctcggaac gtgctggtca agagtcccaa ccatgtcaaa    2580
attacagact tcgggctggc tcggctgctg gacattgacg agacagagta ccatgcagat    2640
gggggcaagg tgcccatcaa gtggatggcg ctggagtcca ttctccgccg gcggttcacc    2700
caccagagtg atgtgtggag ttatggtgtg actgtgtggg agctgatgac ttttggggcc    2760
aaaccttacg atgggatccc agcccgggag atccctgacc tgctggaaaa gggggagcgg    2820
ctgccccagc cccccatctg caccattgat gtctacatga tcatggtcaa atgttggatg    2880
attgactctg aatgtcggcc aagattccgg gagttggtgt ctgaattctc ccgcatggcc    2940
agggacccc agcgctttgt ggtcatccag aatgaggact tgggcccagc cagtcccttg    3000
gacagcacct tctaccgctc actgctggag gacgatgaca tgggggacct ggtggatgct    3060
gaggagtatc tggtacccca gcagggcttc ttctgtccag accctgcccc gggcgctggg    3120
ggcatggtcc accacaggca ccgcagctca tctaccagga gtggcggtgg ggacctgaca    3180
ctagggctgg agccctctga agaggaggcc cccaggtctc cactggcacc ctccgaaggg    3240
gctggctccg atgtatttga tggtgacctg ggaatggggg cagccaaggg gctgcaaagc    3300
ctccccacac atgacccag ccctctacag cggtacagtg aggacccac agtaccctg    3360
ccctctgaga ctgatggcta cgttgccccc ctgacctgca gcccccagcc tgaatatgtg    3420
aaccagccag atgttcggcc ccagcccct tcgccccgag agggccctct gcctgctgcc    3480
cgacctgctg gtgccactct ggaaaggccc aagactctct ccccagggaa gaatggggtc    3540
gtcaaagacg tttttgcctt tgggggtgcc gtggagaacc ccgagtactt gacaccccag    3600
ggaggagctg cccctcagcc ccaccctcct cctgccttca gccagccttc gacaacctc    3660
tattactggg accaggaccc accagagcgg ggggctccac ccagcacctt caaagggaca    3720
cctacggcag agaacccaga gtacctgggt ctggacgtgc cagtg                    3765
```